(12) United States Patent
Valacich et al.

(10) Patent No.: US 10,248,804 B2
(45) Date of Patent: Apr. 2, 2019

(54) FRAUDULENT APPLICATION DETECTION SYSTEM AND METHOD OF USE

(71) Applicants: Arizona Board of Regents on Behalf of University of Arizona, Tucson, AZ (US); Brigham Young University, Provo, UT (US)

(72) Inventors: Joseph Valacich, Tucson, AZ (US); Jeffrey Jenkins, Provo, UT (US)

(73) Assignees: THE ARIZONA BOARD OF REGENTS ON BEHALF OF THE UNIVERSITY OF ARIZONA, Tucson, AZ (US); BRIGHAM YOUNG UNIVERSITY, Provo, UT (US)

( * ) Notice: Subject to any disclaimer, the term of this patent is extended or adjusted under 35 U.S.C. 154(b) by 51 days.

(21) Appl. No.: 15/109,623

(22) PCT Filed: Jan. 30, 2015

(86) PCT No.: PCT/US2015/013706
§ 371 (c)(1),
(2) Date: Jul. 1, 2016

(87) PCT Pub. No.: WO2015/116905
PCT Pub. Date: Aug. 6, 2015

(65) Prior Publication Data
US 2016/0328572 A1    Nov. 10, 2016

Related U.S. Application Data

(60) Provisional application No. 61/934,005, filed on Jan. 31, 2014.

(51) Int. Cl.
*G06F 21/62* (2013.01)
*A61B 5/00* (2006.01)
(Continued)

(52) U.S. Cl.
CPC .......... *G06F 21/6218* (2013.01); *A61B 5/164* (2013.01); *A61B 5/7475* (2013.01); *G06F 21/32* (2013.01); *G06Q 10/10* (2013.01)

(58) Field of Classification Search
None
See application file for complete search history.

(56) References Cited

U.S. PATENT DOCUMENTS

| 8,230,232 | B2* | 7/2012 | Ahmed | ............ G06F 21/36 713/186 |
|---|---|---|---|---|
| 2006/0224898 | A1* | 10/2006 | Ahmed | ............ G06F 21/316 713/186 |
| 2007/0191691 | A1* | 8/2007 | Polanco | ............ A61B 5/0484 600/301 |

OTHER PUBLICATIONS

Jensen et al., Proceedings of the Rapid Screening Technologies Deception and Credibility Assessment Symposium (Jan. 2013).*
(Continued)

*Primary Examiner* — William J. Goodchild
(74) *Attorney, Agent, or Firm* — Blank Rome LLP

(57) ABSTRACT

The present invention provides a system and a method for detecting or determining possible fraudulent information provided by a subject using the subject's behavioral biometric during an application filing process using an electronic input device. The method involves comparing the subject's electronic input device usage characteristic with a control electronic input device usage characteristic data to determine a fraud potential of the subject's input or answer to the question.

17 Claims, 1 Drawing Sheet

(51) Int. Cl.
*A61B 5/16* (2006.01)
*G06F 21/32* (2013.01)
*G06Q 10/10* (2012.01)

(56) References Cited

OTHER PUBLICATIONS

Jenkins et al., Proceedings of the Rapid Screening Technologies Deception and Credibility Assessment Symposium (Jan. 2013) Assessing Credibility by Monitoring Changes in Typing Behavior: The Keystroke Dynamics Deception Detection Model (Year: 2013).*

* cited by examiner

Example Visa
Application

Name

Address

City                                State            Zip

Will you be in the country for longer than 3 months?   Yes    No

Are you transporting any prohibited items?   Yes    No

Region 7 →

What is the purpose of your visit

FRAUDULENT APPLICATION DETECTION SYSTEM AND METHOD OF USE

FIELD OF THE INVENTION

The present invention relates to a system and a method of detecting or determining possible fraudulent information provided by a subject using the subject's behavioral biometric during an application filing process using an electronic input device.

BACKGROUND OF THE INVENTION

The completion of online and paper-based forms is the catalyst for countless business and governmental processes. Examples include, but are not limited to, Visa applications, credit card applications, bank account applications, insurance claims, job and loan applications to name a few.

Current method for determining the veracity of information provided by a subject requires extensive background checking. However, due to inter alia time and economic constraints, majority of information cannot be thoroughly checked.

Therefore, there is a need for a simple method for identifying or determining whether the information provided by a subject is truthful or possibly fraudulent.

SUMMARY OF THE INVENTION

Some aspects of the invention provide a system and a method for detecting anomalous behavior of a subject during an application filling and/or filing process using an electronic input device. Such information can be used to determine whether the information provided by the subject is truthful or possibly fraudulent. Systems and methods of the invention are based at least in part on human-computer interaction data (i.e., input device usage characteristics, e.g., mouse and keyboard activities) to identify anomalous behavior that can be used to determine the likelihood of information provided by a subject being fraudulent.

One particular aspect of the invention provides a system and a method for detecting anomalous behavior by a subject. The system of the invention comprises a behavioral biometric-based analysis system. Generally, the behavioral biometric-based analysis system monitors how the subject uses input device(s). Some aspects of determining how to obtain behavioral biometric of a user is disclosed in U.S. Pat. No. 8,230,232, issued to Ahmed et al., and in commonly assigned U.S. Provisional Patent Application No. 61/837,153, filed Jun. 19, 2013, 61/838,143, filed Jun. 21, 2013, and 61/838,149, filed Jun. 21, 2013, all of which are incorporated herein by reference in their entirety.

Some aspects of the invention provide what is sometimes referred to herein as the "Fraudulent Application Detection System (or FADS)." FADS is a computer or web-based form delivery system that also captures electronic input device dynamics, for example, keyboard dynamics such as the detailed timing information that describes exactly when each key was pressed and when it was released as a person is typing at a computer keyboard; and input device dynamics (e.g., mouse, touch pad, touch screen, joystick, motion sensor, camera, etc.) such as the detailed behavior with a computer-based pointing device.

In particular, some aspects of the invention are based on the discovery by the present inventors that electronic input device (e.g., keyboard, mouse, camera, etc.) dynamics can be used to determine deception by a subject. Accordingly, systems and methods of the invention can identify when a person deceptively answers specific questions on a computer or other electronic input device-based form by analyzing subject's electronic input device (e.g., keyboard, pointing-device, camera, etc.) dynamics. In some embodiments, systems and methods of the invention detect when a person reveals cues of deception when answering specific questions. Such information can be used to guide online or human interview protocols to further assess a person's veracity.

BRIEF DESCRIPTION OF THE DRAWINGS

FIG. 1 is an example of questionnaire form for an online visa application.

DETAILED DESCRIPTION OF THE INVENTION

The present inventors' research on deception has established that humans have uncontrolled physiological changes (e.g., cognitive conflict and arousal) that can be detected as observable behavioral changes when committing actions known to be outside the norm, immoral, criminal, or unethical. One of the possible catalysts for creating an uncontrolled physiological response in a person is online and/or computer activity, in particular when a subject fills out or provides false information on an application. As used herein, the term "application" includes any computer- or online-based questionnaires requiring input from a subject such as, but not limited to, Visa applications, immigration forms, credit card applications, bank account applications, insurance claims, job applications, loan applications, etc.

One aspect of the invention is based on the discovery that deception which often results in hesitation and/or heightened emotion and/or stress can be detected through subtle behavioral changes captured by anomalous electronic input device (e.g., keyboard, mouse, pointing device, joystick, motion sensor, camera, etc.) usage patterns. In some embodiments, to identify a possible deception or fraudulent information, the behavioral biometric-based analysis system is designed to develop baselines or control input device usage characteristics for each user by longitudinally collecting and analyzing electronic input device usage characteristics (e.g., keystroke, mouse movement patterns, etc.), e.g., for benign inquiries. Alternatively, or in addition, electronic input device usage characteristics (or control input device usage characteristics) can be established for a large sample of subjects who have truthfully answered inquiries. Still alternatively or in addition, electronic input device usage characteristics can be established for a large sample of subjects who have fraudulently answered inquiries. These "baseline" electronic input device usage characteristics are termed "control electronic input device usage characteristic data" or simply "control electronic input device usage characteristics." The control electronic input device usage characteristics can be a range or a median±a standard deviation or within certain percentage (e.g., within ±60%, ±75%, ±80%, and/or ±90%) of the median.

Over time, control electronic input device usage characteristic data can be updated and refined as a person's behavior and usage increases or as more data is gathered from additional people. Thus, in some embodiments, the control electronic input device usage characteristic data is dynamically updated. Once control electronic input device usage characteristic data have been developed, systems and methods of the invention detect when anomalous patterns and/or a possible deception has occurred.

In some embodiments, all information associated with subject's electronic input device usage characteristics are contextually and continuously monitored. The term "contextually monitored" refers to analyzing the electronic input device usage characteristics of the subject for a given inquiry. The term "electronic input device usage characteristics" refers to how and the way (or method of) a particular electronic input device (e.g., keyboard, a pointing-device, etc.) is used by the subject. In general, "how" a subject uses an electronic input device can be objectively measured and includes, without limitation, the duration of keyboard press, pressure applied to a keyboard when typing, keyboard stroke speed, the dwell time (the length of time a key is held down) and flight time (the time to move from one key to another) for keyboard actions, etc. The term "way" of using an electronic input device refers to how a particular function or answer is selected, e.g., whether a keyboard or a mouse is used for a particular inquiry; whether the subject uses a numeric keypad or the number keys across the top of the keyboard, whether the subject changes the answer, how many times the answers are changed, whether the subject answers an inquiry and subsequently goes back to a previously answered query, etc.

Online Human Behavioral Sensor Monitoring:

Cognitive psychology research has demonstrated that deceptive behavior results in increased mental workload and heightened emotion. These increases in mental workload and emotion are manifested in uncontrolled physiological changes that can be detected through subtle changes to electronic input device usage characteristics (e.g., keystroke, mouse usage behavior, etc.). When developing behavioral baselines (i.e., control electronic input device usage characteristics) in order to detect possibly deceptive answer, an electronic input device (e.g., mouse and/or keyboard) usage data is collected over time so that a comprehensive behavioral pattern or usage characteristics is developed for various critical online inquiries. By comparing anomalous behavior to robust baselines or dynamic usage characteristics based on the context and inquiries the subject is answering, systems and methods of the invention are able to identify instances in which a subject's answer to an inquiry may be false or misleading.

System Implementation and Management Dashboard:

In some embodiments, systems and methods of the invention are capable of real-time monitoring of subject's electronic input device usage characteristics (or "behavioral biometrics"). Systems and methods of the invention can continuously, typically passively, monitor subject's electronic input device (e.g., mouse, keyboard, touch screen, camera, etc.) usage characteristics and send such information to the system server for analysis either in real-time as the samples are taken or when the inquiries are completed.

When the analysis of subject's behavioral biometrics shows difference compared to the control electronic input device usage characteristic data (or "control biometrics") for a particular inquiry or question, it indicates a possible fraudulent response by the subject. In such cases, an appropriate action can be taken with respect to such inquiry. For example, the subject can be personally interviewed or further inquiries can be made for that particular question, and so on.

One particular aspect of the invention provides a fraud detection method during an electronic application filling process by a subject. Such a method typically comprises:

(i) passively collecting an electronic input device usage characteristic of a subject during said subject's electronic application filing process; and (ii) determining a fraud potential of said subject by comparing said subject's electronic input device usage characteristic with a control electronic input device usage characteristic data.

In some embodiments, said control electronic input device usage characteristic data comprises electronic input device usage characteristic data of non-fraudulent subjects, and wherein a difference in said subject's electronic input device usage characteristic compared to said control electronic input device usage characteristic data is an indication of potential fraud by said subject.

Yet in other embodiments, said control electronic input device usage characteristic data comprises electronic input device usage characteristic data of fraudulent subjects, and wherein no significant difference in said subject's electronic input device usage characteristic compared to said control electronic input device usage characteristic data is an indication of potential fraud by said subject.

Still in other embodiments, said subject's electronic input device usage characteristic is collected for each section of information (e.g., question or field on a form), and wherein said subject's electronic input device usage characteristic for each information represents a different behavioral biometric measurement for said subject in a set of subject's behavioral biometric measurements. Within these embodiments, in some instances said control electronic input device usage characteristic data comprises said set of subject's behavioral biometrics excluding said subjects biometric for information being evaluated for fraud.

In some instances a statistically significant difference in electronic input device usage characteristic data is an indication of potential fraud by said subject. The term "statistically significant difference" refers to p-value of at least 0.1, typically at least 0.05 and often at least 0.01. In other instances, a meaningful difference in electronic input device usage characteristic data is an indication of potential fraud by said subject. The term "meaningful difference" means that it may help discriminate between truthful and deceptive responses in a prediction model, or it may not be statistically significant (or p-value of >0.1 but less than 0.5) but the difference in the electronic input device usage characteristic data increases the prediction rate between truth and deception in a prediction algorithm.

Other aspects of the invention provide a fraud detection system comprising a digital processor configured to implement a fraud detection method disclosed herein. In some embodiment, the system includes hardware logic means arranged to implement one or more steps in the fraud detection method in hardware and to interact with the digital processor in an implementation of such method. Often, however, the method is implemented into the system as a loadable or downloadable software. Typically, this software runs passively in the background Still other aspects of the invention provide a computer program product comprising a computer-readable medium having stored thereon software code means which when loaded and executed on a computer implements a fraud detection method disclosed herein. As used herein, the "computer-readable medium" refers to any recordable and/or readable medium known to one skilled in the art or developed hereinafter such as, but not limited to, CD, DVD, flash-drive, hard drive, etc.

Yet other aspects of the invention provide a fraud detection system for determining a potential for fraudulent information input by a subject during an electronic information input process, said system comprising:
　　a behavioral biometric-based analysis system comprising:
　　　(i) a data input interception unit configured to intercept a subject's information input in response to a query using an electronic input device, wherein the data interception unit is configured to collect an electronic input device usage characteristic;
　　　(ii) a behavior analysis unit operatively coupled to said data interception unit to receive the collected input device usage characteristic; and
　　　(iii) a behavior comparison unit operatively coupled to said behavior analysis unit,
wherein said behavioral biometric-based analysis system monitors and collects behavioral biometric information of said subject using said electronic input device during an electronic information input process, and translates said behavioral biometric information into a representative data and said behavior comparison unit compares said representative data with a control data set and outputs a behavioral biometric-based analysis result associated with behavior of said subject, thereby identifying a potentially fraudulent information input by said subject.

In some embodiments, said data interception unit is configured to passively collect said subject's electronic input device usage characteristic. Within these embodiments, in some instances said behavioral biometric-based analysis system dynamically monitors and passively collects behavioral biometric information of said subject's electronic input device usage characteristic.

Still in other embodiments, said behavioral biometric-based analysis system is further configured to store said representative data with a control data set, and outputs a behavioral biometric-based analysis result associated with behavior of the subject to thereby identify a potential deception by the subject.

Yet in other embodiments, said electronic input device comprises a keyboard, mouse, a touch pad, a touch screen, a stylus, a microphone, a track ball, a pointer device, a remote or embedded camera (e.g., webcam), a joy stick, a movement sensor (e.g., XBOX® Kinect and LEAP MOTION® Controller) or a combination thereof.

In other embodiments, said data interception unit is configured to passively collect said subject's electronic input device usage characteristics comprising how and the way said subject uses said electronic input device.

Still yet in other embodiments, said system is suitably configured for real-time monitoring.

Yet still further, in other embodiments said system is suitably configured for post-input processing. In this embodiment, such system is configured for after-the-fact analysis of data. For example, when the subject submits the application after filling it out (e.g., in an electronic form such as a portable document format or "pdf"), the collected electronic input device usage characteristic data associated with each inquiry within the application is submitted together with the form unbeknownst to the subject. The recipient then can analyze the subject's electronic input device usage characteristic data to look for potentially fraudulent answers. As can be appreciated, in these embodiments, the electronic input device usage characteristic data collection process is implemented within or in addition to the inquiry program.

In some embodiments, subject's electronic input device usage characteristic data include at least ten, typically at least twenty, often at least thirty, and most often all of the characteristics disclosed in Table 1 below.

FADS—Fraudulent Application Detection System:

The completion of online and paper-based forms is the catalyst for countless business and governmental processes. Examples include Visa applications, insurance claims, job applications, and loan applications to name a few. The Fraudulent Application Detection System (FADS) is a technology that can be administered online in survey administration systems, integrated with other $3^{rd}$ party systems, or embedded in an online or offline file (e.g., a PDF) that also captures (1) keyboard dynamics—the detailed timing information that describes, for example, exactly when each key was pressed, when it was released, how long the key was pressed, etc., as a person is typing at a computer keyboard; and (2) pointing device dynamics (mouse, touch pad, touch screen, etc.)—the detailed behavior with a computer-based pointing device.

Some aspects of the invention are based on the discovery by the present inventors that keyboard and mouse dynamics can predict deception. In some embodiments, methods and systems of the invention can identify when a person deceptively answers specific questions on a computer-based form by analyzing keyboard- and/or pointing-device dynamics. Because methods and systems of the invention can detect when a person reveals cues of deception in answering specific questions, methods and systems of the invention can guide online or human interview protocols to further assess a person's veracity.

Functionality:

In some embodiments, FADS is a software program that detects deception while a person fills out an electronic form on a computer. However, it should be appreciated that some portions or all of FADS can be hardware based. That is, methods of the invention can be permanently programmed (e.g., on EPRAM, or ROM) onto the hardware. As an example, in filling out a Visa application to visit a foreign country, a person may need to answer several questions that identify oneself and disclose one's intentions. Such questions may include one's name and address, how long the person plans to stay in the country, the purpose of the visit, and whether the person is transporting any prohibited items, to name a few. When answering these questions, FADS can detect when someone may be answering falsely (e.g., lying) or contemplating a false answer or lying in the application. FADS achieves this by passively monitoring subject's usage characteristics of input devices (e.g., the mouse, touchpad, touchscreen, keyboard, etc.). In some embodiments, in addition to monitoring the overall behavior on the application, FADS is configured to also associate these movements and keystrokes with regions on the page that are associated with specific questions (e.g., specific areas that surround a question). For example, in FIG. 1, FADS not only captures a person's movements and keystrokes on the entire application in general, but also knows (e.g., analyzes, determines or associates) the movements and keystrokes that are associated with a given question.

In some embodiments, FADS also records behavior data of the person filling out the application. For example, FADS records each time a person answers a question, and what the person answered. Thus, if someone changes an answer on the application, in some embodiments the system is configured to record both the original answer and the modified answer. Furthermore, in other embodiments, FADS is configured to also record when people hover over each answer (e.g., the amount of time a subject hovers over an answer or a simply true/false condition), thereby indicating when a user is considering changing an answer or when a user revisits a question after having already answered it. For example, in one particular embodiment, if a person originally clicks on the option "Yes" for "Will you be in the country for longer than 3 months?", then changes the answer to "No", and then again returns to read the question after answering a few other questions, FADS records that the answer has changed as well as what the previous answer was, and FADS also records that the person hovered over the question while reading it again after answering other questions.

In other embodiments, for the page in general and for each region, FADS is configured to utilize the pointing device movement, keystroke, and/or behavioral data to generate a number of statistics that is used to determine or detect deception. Some of the characteristics that can be utilized to detect or determine deception include, but are not limited to, the characteristics listed in Table 1 below.

TABLE 1

Example Movement, Keystroke, and Behavioral Statistics Captured and Calculated for Each Region and for the Page in General

| Statistic | Description |
| --- | --- |
| X | The X coordinates for each movement |
| Y | The Y coordinates for each movement |
| Z | The Z coordinate for each movement |
| Pressure | The pressure for each movement |
| Re scaled X | The X coordinates for the interaction normalized for screen resolution |
| Rescaled Y | The Y coordinates for the interaction normalized for screen resolution |
| X Average | The X coordinates averaged in buckets of 75 msec |
| Y Average | The Y coordinates averaged in buckets of 75 msec |
| X Norm | The X coordinates time normalized |
| Y Norm | The Y coordinates time normalized |
| Pressure | The pressure applied to the mouse for every raw recording |
| Timestamps | The timestamp for every raw recording |
| Click Direction | Whether the mouse button was pushed down (d) or released (u) for every time an action occurred with the mouse button |
| Click X | The X coordinates for each mouse click event |
| Click Y | The Y coordinates for each mouse click event |
| Click Rescaled X | The X coordinates for each mouse click event normalized for screen resolution |
| Click Rescaled Y | The Y coordinates for each mouse click event normalized for screen resolution |
| Click Pressure | The pressure applied to the mouse for every raw recording |
| Click timestamps | The timestamp for every mouse click event |
| Acceleration | The average acceleration for each 75 msec |
| Angle | The average angle for each 75 msec |
| Area Under the Curve (AUC) | The geometric area between the actual mouse trajectory and the idealized response trajectory (i.e., straight lines between users' mouse clicks); it is a measure of total deviation from the idealized trajectory. |
| Additional AUC | The AUC minus the minimum AUC |
| Additional AUC normalized by distance | The AUC minus the minimum AUC divided by the length of the normalized response trajectory |
| Overall Distance | The total distance traveled by the mouse trajectory |
| Additional Distance | The distance a users' mouse cursor traveled on the screen minus the distance that it would have required to traveling along the idealized response trajectory (i.e. straight lines between users' mouse clicks), |
| Distance Additional Normalized by Distance | The distance a users' mouse cursor traveled on the screen minus the distance that it would have required to traveling along the idealized response trajectory (i.e. straight lines between users' mouse clicks), divided by the total distance of the idealized response trajectory |
| Distance Buckets | Distance traveled for each 75 msec |
| X Flips | The number of reversals on the x axis |
| Y Flips | The number of reversals on the y axis |
| Maximum Deviation | The largest perpendicular deviation between the actual trajectory and its idealized response trajectory (i.e., straight lines between users' mouse clicks), |
| Speed Buckets | Average speed for each 75 msec |
| Overall Speed | Average overall speed |
| Idle Time | if there is a change in time greater than 200 msec but no movement, this is counted as idle time |
| Initial Idle Time | The amount of idle time before a person starts moving |
| Idle Time on Same Location | If there is a change in time but not a change in location, this mean an event other than movement triggered a recording (e.g., such as leaving the page, and other things). The time in this event is summed. |
| Idle Time On 100 Distance | If there is a change in distance greater than 100 between two points, this may indicate that someone left the screen and came back in another area |
| Total Time | Total response time |
| Click Mean Speed | The mean speed of users click |
| Click Median Speed | The median speed of users click |
| Click Mean Latency | The mean time between when a user clicks down and releases the click |
| Click Median Latency | The median time between when a user clicks down and releases the click |
| Graded Motor Response | The total amount of deviation from the idealized response trajectory for a given time period or portion of a persons' movement. |

TABLE 1-continued

Example Movement, Keystroke, and Behavioral Statistics Captured
and Calculated for Each Region and for the Page in General

| Statistic | Description |
| --- | --- |
| Answer Changes | The number of times an answer was selected; if over 1, the person changed answers |
| Hover Changes | The number of times an answer was hovered; if over 1, the person hovered over answers they didn't chose |
| Hover Region | The amount of time a person overs over a region |
| Return Sum | The number of times a person returns to a region after leaving it |
| Dwell | The measurement of how long a key is held down |
| Transition | Time between key presses |
| Rollover | The time between when one key is released and the subsequent key is pushed |

In some embodiments, FADS generates a baseline model for both the individual and the population of people filling out the same or similar type of questions on the form. Based on this model, FADS is able to predict the normal movement, keystroke, and behavioral responses for each question. Likewise, FADS can detect anomalous movements that show signs of a possible deception. Based on these anomaly calculations and verified cues of deception (discussed infra), FADS generates a confidence score for each answer. Low confidence scores for questions indicate that the person filling out may be or is likely lying to those questions, and vice versa.

Yet in another aspect, the fraudulent application detection system (FADS) of the invention has three or more, typically at least five, often at least seven, more often at least nine, and most often all of the following functionalities:

1) Embedded in online or offline systems and files.
2) Monitor all movements from an input device (e.g., the mouse, touchpad, touchscreen etc.) and keystrokes from the keyboard on a page containing a form
3) Specify regions on a page that correspond to specific questions on the form
4) Associate movements and keystrokes on the page to a specific region
5) Use logic to determine which question on the page a person is answering.
6) Associate movement and keystrokes on a page to a specific question.
7) Record each time when an answer was selected and deselected in the form for specific questions and regions
8) Record when a user hovers over different answers and regions in the form
9) Based on this input data, calculate movement, keystroke, and behavioral statistics for each region and for the aggregate form (See Table 1).
10) Identify within subject anomalies (e.g., behavior that was abnormal for a question based on an individual baseline)
11) Identify between subject anomalies (e.g., behavior that was abnormal for a question based on a population baseline)
12) Calculate a risk/confidence score based on said anomalies.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Validated Cues

The present inventors have established validated cues of deception while people fill out online forms and provide online information. Some of these cues are based on the statistics shown in Table 1 above, and selected examples are described below. Overall, the present inventors have conducted studies with over 6,000 human subjects to understand how movement and keystroke behavior reflect people's thoughts and cognitions that may be related to deception (e.g., cognitive conflict, stress, arousal, indecision, etc.). For example, in a study that explored fraud in insurance applications, the statistics listed in Table 2 differentiated between people who were truthful and people who committed fraud. In another study on measuring decision conflict (a common indicator of deception), when experiencing conflict on how to answer, click latency increases substantially: people experiencing little cognitive conflict while answering online questions had a mean click latency between 42.4 and 162.5 msec. The people who were experiencing cognitive conflict while answering online questions had a click latency over 162.5 msec.

TABLE 2

Example Movement, Keystroke, and Behavioral Statistics Captured
and Calculated for Each Region and for the Page in General

| Statistic | Description |
| --- | --- |
| X Average | The X coordinates averaged in buckets of 75 msec |
| Y Average | The Y coordinates averaged in buckets of 75 msec |
| X Norm | The X coordinates time normalized |
| Y Norm | The Y coordinates time normalized |
| Acceleration | The average acceleration for each 75 msec |

TABLE 2-continued

Example Movement, Keystroke, and Behavioral Statistics Captured
and Calculated for Each Region and for the Page in General

| Statistic | Description |
| --- | --- |
| Angle | The average angle for each 75 msec |
| Area Under the Curve (AUC) | The geometric area between the actual mouse trajectory and the idealized response trajectory (i.e., straight lines between users' mouse clicks); it is a measure of total deviation from the idealized trajectory. |
| Additional AUC | The AUC minimum the minimum AUC |
| Overall Distance | The total distance traveled by the mouse trajectory |
| Additional Distance | The distance a users' mouse cursor traveled on the screen minus the distance that it would have required to traveling along the idealized response trajectory (i.e. straight lines between users' mouse clicks), |
| Distance Buckets | Distance traveled for each 75 msec |
| X Flips | The number of reversals on the x axis |
| Y Flips | The number of reversals on the y axis |
| Maximum Deviation | The largest perpendicular deviation between the actual trajectory and its idealized response trajectory (i.e., straight lines between users' mouse clicks), |
| Speed Buckets | Average speed for each 75 msec |
| Overall Speed | Average overall speed |
| Idle Time | if there is a change in time greater than 200 msec but no movement, this is counted as idle time |
| Initial Idle Time | The amount of idle time before a person starts moving |
| Total Time | Total response time |
| Click Mean Latency | The mean time between when a user clicks down and releases the click |
| Click Median Latency | The median time between when a user clicks down and releases the click |
| Graded Motor Response | The total amount of deviation from the idealized response trajectory for a given time period or portion of a persons' movement. |
| Answer Changes | The number of times an answer was selected; if over 1, the person changed answers |
| Hover Changes | The number of times an answer was hovered; if over 1, the person hovered over answers they didn't chose |

The present inventors have also found that when people experience cognitive conflict, arousal, or negative valence (which are by-products of deception), their fine-motor movement precision (e.g., movement of the hand and fingers) decreases. These minute changes in precision can clearly be observed through recording and analyzing mouse movements at a millisecond precision rate. Some of the mousing statistics that were utilized to measure movement precision are X- and Y-Flips, Maximum Deviation (MD), Area under the Curve (AUC), Additional Distance (AD), Speed and Acceleration. The results of one experiment are shown below. As can be seen, when experiencing cognitive conflict, highly significant differences are seen in mousing behavior. These and dozens of other studies that have revealed many other cues of deception have resulted in a rich set of movement, keystroke, and behavioral statistics that are used to predict deception in online surveys.

TABLE 3

Sample Results from an Experiment

| Measure | High Cognitive Conflict (Mean) | High Cognitive Conflict (SD) | Baseline Condition (Mean) | Baseline Condition (SD) | $t_{(df)}$ | P |
| --- | --- | --- | --- | --- | --- | --- |
| AUC | 8.281 | 6.731 | 14.660 | 11.148 | $3.888_{(124)}$ | <.001 |
| AD | 19.349 | 13.125 | 35.314 | 22.974 | $4.789_{(124)}$ | <.001 |
| MD | 3.470 | 1.371 | 3.956 | 1.580 | $1.843_{(124)}$ | <.001 |
| x- and y-flips | 60.079 | 30.291 | 110.524 | 67.786 | $4.324_{(124)}$ | <.05 |

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A real-time fraud detection method during data entry in an electronic application filing process by a subject, said method comprising:
   passively collecting in real-time an electronic input device usage characteristic of a subject during said subject's data entry in an electronic application filing process;
   (ii) calculating a confidence score against a baseline model comprised of both the subject's electronic input device usage characteristic data and population input device usage characteristic data; and (iii) on the basis of the confidence score, determining in real-time a fraud potential of said subject by comparing said subject's electronic input device usage characteristic data with a control electronic input device usage characteristic data.

2. The method of claim 1, wherein said control electronic input device usage characteristic data comprises electronic input device usage characteristic data of non-fraudulent subjects, and wherein a difference in said subject's electronic input device usage characteristic data compared to said control electronic input device usage characteristic data is an indication of potential fraud by said subject.

3. The method of claim 1, wherein said control electronic input device usage characteristic data comprises electronic input device usage characteristic data of fraudulent subjects, and wherein no significant difference in said subject's electronic input device usage characteristic data compared to said control electronic input device usage characteristic data is an indication of potential fraud by said subject.

4. The method of claim 1, wherein said subject's electronic input device usage characteristic data is collected for each piece or type of information, and wherein said subject's electronic input device usage characteristic data for each piece of information represents a different behavioral biometric for said subject in a set of subject's behavioral biometrics.

5. The method of claim 4, wherein said control electronic input device usage characteristic data comprises said set of subject's behavioral biometrics excluding said subjects behavioral biometric for information being evaluated for fraud.

6. A fraud detection system for determining a potential for fraudulent information input by a subject during an electronic information input process, said system comprising:
a behavioral biometric-based analysis system comprising:
(i) a data input interception unit configured to intercept a subject's information input in response to a query using an electronic input device, wherein the data interception unit is configured to collect an electronic input device usage characteristic;
(ii) a behavior analysis unit operatively coupled to said data interception unit to receive the collected input device usage characteristic; and
(iii) a behavior comparison unit operatively coupled to said behavior analysis unit that calculates a confidence score against a baseline model comprised of control data, wherein the control data is comprised of both the subject's electronic input device usage characteristic data and population input device usage characteristic data, wherein said behavioral biometric-based analysis system monitors and collects behavioral biometric information of said subject using said electronic input device during an electronic information input process, and translates said behavioral biometric information into a representative data and said behavior comparison unit compares said representative data with a control data set and outputs a behavioral biometric-based analysis result associated with behavior of said subject, thereby identifying a potentially fraudulent information input by said subject.

7. The system of claim 6, wherein said data interception unit is configured to passively collect said subject's electronic input device usage characteristic data.

8. The system of claim 7, wherein said behavioral biometric-based analysis system dynamically monitors and passively collects behavioral biometric information of said subject's electronic input device usage characteristic data.

9. The system of claim 6, wherein said behavioral biometric-based analysis system is further configured to store said representative data with a control data set, and outputs a behavioral biometric-based analysis result associated with behavior of the subject to thereby identify a potential deception by the subject.

10. The system of claim 6, wherein said electronic input device comprises a keyboard, mouse, a touch pad, a touch screen, a stylus, a microphone, a track ball, pointer device, a remote camera, a joy stick, a movement sensor or a combination thereof.

11. The system of claim 6, wherein said data interception unit is configured to passively collect said subject's electronic input device usage characteristic data comprising how and the way said subject uses said electronic input device.

12. The system of claim 6, wherein said system is suitably configured for real-time monitoring.

13. A real-time fraud detection system comprising:
a central processing unit operatively connected to an input device and configured to passively collect an input device usage characteristic in real-time during a subject's use of said system in data entry during an application filing process; and
a data analysis unit for comparing the subject's electronic input device usage characteristic data with a control electronic input device usage characteristic data in real-time to determine a fraud potential of the subject, wherein the fraud potential is determined as a confidence score against a baseline model comprising both the subject's electronic input device usage characteristic data and population input device usage characteristic data.

14. The system of claim 13, wherein the input usage characteristic comprises electronic input device usage characteristic data of non-fraudulent subjects, and wherein a difference in said subject's electronic input device usage characteristic compared to said control electronic input device usage characteristic data is an indication of potential fraud by said subject.

15. The system of claim 13, wherein behavioral biometric information of the subject's electronic input device usage characteristic data is collected.

16. The system of claim 13, wherein the electronic input device comprises a keyboard, mouse, a touch pad, a touch screen, a stylus, a microphone, a track ball, pointer device, a remote camera, a joy stick, a movement sensor or a combination thereof.

17. The system of claim 13, wherein the control electronic input device usage characteristic data comprises electronic input device usage characteristic data of non-fraudulent subjects, and wherein a difference in the subject's electronic input device usage characteristic data compared to said control electronic input device usage characteristic data is an indication of potential fraud by the subject.

* * * * *